US00PP25208P2

(12) United States Plant Patent
Misato

(10) Patent No.: US PP25,208 P2
(45) Date of Patent: Jan. 6, 2015

(54) ***MANDEVILLA* PLANT NAMED 'SUNPARAOCHOCO'**

(50) Latin Name: *Mandevilla hybrida*
Varietal Denomination: Sunparaochoco

(71) Applicant: Tomoya Misato, Shiga (JP)

(72) Inventor: Tomoya Misato, Shiga (JP)

(73) Assignee: Suntory Flowers Ltd., Tokyo (JP)

( * ) Notice: Subject to any disclaimer, the term of this patent is extended or adjusted under 35 U.S.C. 154(b) by 111 days.

(21) Appl. No.: 13/815,176

(22) Filed: Feb. 5, 2013

(51) Int. Cl.
*A01H 5/00* (2006.01)

(52) U.S. Cl.
USPC ..... Plt./232

(58) Field of Classification Search
USPC ..... Plt./232
See application file for complete search history.

*Primary Examiner* — Susan McCormick Ewoldt
(74) *Attorney, Agent, or Firm* — C. A. Whealy

(57) ABSTRACT

A new and distinct cultivar of *Mandevilla* plant named 'Sunparaochoco', characterized by its compact and vining plant habit; vigorous growth habit; freely branching habit, dense and bushy plant form; dark green-colored leaves; freely flowering habit; long flowering period; and medium-sized dark red purple-colored flowers.

1 Drawing Sheet

Botanical designation: *Mandevilla hybrida.*
Cultivar denomination: 'SUNPARAOCHOCO'.

BACKGROUND OF THE INVENTION

The present invention relates to a new and distinct cultivar of *Mandevilla* plant, botanically known as *Mandevilla hybrida* and hereinafter referred to by the name 'Sunparaochoco'.

The new *Mandevilla* plant is a product of a planned breeding program conducted by the Inventor in Higashiomi, Shiga, Japan. The objective of the breeding program is to create new compact, freely-branching and vining *Mandevilla* plants with numerous medium-sized attractive flowers.

The new *Mandevilla* plant originated from a cross-pollination in Higashiomi, Shiga, Japan in April, 2006 of a proprietary selection of *Mandevilla hybrida* identified as code number 02M11-1, not patented, as the female, or seed parent with a proprietary selection of *Mandevilla hybrida* identified as code number M37-mt2, not patented, as the male, or pollen, parent. The new *Mandevilla* plant was discovered and selected by the Inventor as a single flowering plant from within the progeny of the stated cross-pollination in a controlled greenhouse environment in Higashiomi, Shiga, Japan in October, 2007.

Asexual reproduction of the new *Mandevilla* plant by cuttings in Higashiomi, Shiga, Japan since October, 2007 has shown that the unique features of this new *Mandevilla* plant are stable and reproduced true to type in successive generations.

SUMMARY OF THE INVENTION

Plants of the new *Mandevilla* have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'Sunparaochoco'. These characteristics in combination distinguish 'Sunparaochoco' as a new and distinct *Mandevilla* plant:

1. Compact and vining plant habit.
2. Vigorous growth habit.
3. Freely branching habit, dense and bushy plant form.
4. Dark green-colored leaves.
5. Freely flowering habit.
6. Long flowering period.
7. Medium-sized dark red purple-colored flowers.

Plants of the new *Mandevilla* can be compared to plants of the female parent selection. Plants of the new *Mandevilla* differ primarily from plants of the female parent selection in the following characteristics:

1. Plants of the new *Mandevilla* are more compact than plants of the female parent selection.
2. Plants of the new *Mandevilla* have shorter lateral branches with shorter internodes than plants of the female parent selection.
3. Plants of the new *Mandevilla* and the female parent selection differ in flower color as plants of the female parent selection have dark red-colored flowers.

Plants of the new *Mandevilla* can be compared to plants of the male parent selection. Plants of the new *Mandevilla* differ primarily from plants of the male parent selection in the following characteristics:

1. Plants of the new *Mandevilla* are not as compact as plants of the male parent selection.
2. Plants of the new *Mandevilla* have longer lateral branches with longer internodes than plants of the male parent selection.
3. Plants of the new *Mandevilla* and the male parent selection differ in flower color as plants of the male parent selection have light pink-colored flowers.

Plants of the new *Mandevilla* can be compared to plants of the *Mandevilla* 'Sunparacore', disclosed in U.S. Plant Pat. No. 23,959. In side-by-side comparisons conducted in Higashiomi, Shiga, Japan, plants of the new *Mandevilla* differed from plants of 'Sunparacore' in the following characteristics:

1. Plants of the new *Mandevilla* had shorter internodes than plants of 'Sunparacore'.
2. Plants of the new *Mandevilla* had smaller leaves than plants of 'Sunparacore'.
3. Plants of the new *Mandevilla* had smaller flowers with narrower petals than plants of 'Sunparacore'.
4. Plants of the new *Mandevilla* and 'Sunparacore' differed in flower color as plants of 'Sunparacore' had dark red-colored flowers.

BRIEF DESCRIPTION OF THE PHOTOGRAPHS

The accompanying colored photographs illustrate the overall appearance of the new *Mandevilla* plant showing the colors as true as it is reasonably possible to obtain in colored reproductions of this type. Colors in the photographs may differ slightly from the color values cited in the detailed botanical description which accurately describe the actual colors of the new *Mandevilla* plant.

The photograph at the top of the sheet comprises a side perspective view of a typical flowering plant of 'Sunparaochoco' grown in a container.

The photograph at the bottom of the sheet is a close-up view of a typical flowering plant of 'Sunparaochoco'.

DETAILED BOTANICAL DESCRIPTION

The aforementioned photographs and following observations, measurements and values describe plants grown during the late summer and early autumn in 15-cm containers in an outdoor nursery in Higashiomi, Shiga, Japan and under cultural practices typical of commercial production. During the production of the plants, day temperatures averaged 25° C. and night temperatures averaged 15° C. Plants were six months old when the photographs and detailed description were taken. In the following description, color references are made to The Royal Horticultural Society Colour Chart, 2007 Edition, except where general terms of ordinary dictionary significance are used.

Botanical classification: *Mandevilla hybrida* 'Sunparaochoco'.

Parentage:

*Female, or seed, parent*.—Proprietary selection of *Mandevilla hybrida* identified as code number 02M11-1, not patented.

*Male, or pollen, parent*.—Proprietary selection of *Mandevilla hybrida* identified as code number M37-mt2, not patented.

Propagation:

*Type*.—By vegetative cuttings.

*Time to initiate roots*.—About two weeks at 23° C. to 25° C.

*Time to produce a rooted young plant*.—About five to six weeks at 23° C. to 25° C.

*Root description*.—Fibrous; light brown in color.

*Rooting habit*.—Freely branching; medium density.

Plant description:

*Plant and growth habit*.—Compact and vining plant habit; vigorous growth habit; freely branching habit.

*Lateral branch description*.—Length: About 129 cm. Diameter: About 1.8 mm. Internode length: About 2.2 cm. Strength: Strong. Texture: Smooth, glabrous. Color: Close to 143B tinted with close to 177B.

Foliage description:

*Arrangement*.—Opposite, simple.

*Length*.—About 5.3 cm.

*Width*.—About 3.1 cm.

*Shape*.—Elliptical.

*Apex*.—Acuminate.

*Base*.—Obtuse.

*Margin*.—Entire; slightly undulate.

*Texture, upper and lower surfaces*.—Pubescent.

*Venation pattern*.—Pinnate, reticulate.

*Color*.—Developing leaves, upper surface: Close to 144A. Developing leaves, lower surface: Close to 144B. Fully expanded leaves, upper surface: Close to N137A; venation, close to 144B. Fully expanded leaves, lower surface: Close to 138A; venation, close to 144C.

*Petiole length*.—About 1.6 cm.

*Petiole diameter*.—About 1.3 mm.

*Petiole texture, upper and lower surfaces*.—Smooth, glabrous.

*Petiole color, upper and lower surfaces*.—Close to 144A.

Flower description:

*Flower type and habit*.—Single salverform flowers arranged in axillary racemes; flowers face upright to outwardly; freely flowering habit with about two to six flowers per inflorescence.

*Natural flowering season*.—Plants begin flowering about six weeks after planting; long flowering period, plants flower continuously from early summer to late autumn in Japan.

*Flower longevity on the plant*.—About seven to ten days; flowers not persistent.

*Fragrance*.—None detected.

*Inflorescence height*.—About 12.6 cm.

*Inflorescence diameter*.—About 15.2 cm.

*Flowers*.—Appearance: Salverform; flared trumpet, corolla fused and five-parted; flowers roughly star-shaped. Diameter: About 7.1 cm. Depth (length): About 7.2 cm. Throat diameter: About 1.6 cm. Tube length: About 5.4 cm. Tube diameter, mid-section: About 1.1 cm. Tube diameter, base: About 3.1 mm.

*Flower buds*.—Height: About 6.6 cm. Diameter: About 1.1 cm. Shape: Lenticular. Color: Close to 187A.

*Corolla*.—Quantity and arrangement: Five petals arranged in a single whorl and fused towards the base into an elongated tube; petals imbricate. Petal lobe length: About 3.5 cm. Petal lobe width: About 2.5 cm. Petal lobe shape: Ovate; asymmetrical. Petal lobe apex: Cuspidate. Petal lobe margin: Entire; slightly undulate. Petal lobe texture, upper and lower surfaces: Smooth, glabrous. Throat texture: Smooth, glabrous. Tube texture: Smooth, glabrous. Color: Petal lobe, when opening, upper and lower surfaces: Close to 187B. Petal lobe, fully opened, upper and lower surfaces: Close to 59A. Throat: Close to N25A; proximally, close to 4C. Tube: Distally, close to 59B; mid-section, close to 4C; proximally, close to 42B.

*Calyx*.—Quantity and arrangement: Five sepals arranged in a single whorl; calyx, star-shaped. Sepal length: About 8 mm. Sepal width: About 1.8 mm. Sepal shape: Deltoid. Sepal apex: Acute. Sepal base: Truncate. Sepal margin: Entire. Sepal texture, upper and lower surfaces: Smooth, glabrous. Sepal color: When developing, upper surface: Close to 143C tinged with close to 178C. When developing, lower surface: Close to 143C. Fully developed, upper surface: Close to 144C tinged with close to 180A. Fully developed, lower surface: Close to 144C.

*Peduncles*.—Length: About 20.4 cm. Diameter: About 1.6 mm. Texture: Smooth, glabrous. Aspect: Obliquely upright. Color: Close to 144A.

*Pedicels*.—Length: About 1.5 cm. Diameter: About 1.8 mm. Texture: Smooth, glabrous. Aspect: Obliquely upright. Color: Close to 144B.

*Reproductive organs*.—Stamens: Quantity and arrangement: Typically five; filaments fused to corolla; anthers, connivent. Anther shape: Ellipsoidal. Anther size: About 8.8 mm by 1.8 mm. Anther color: Close to 8B; apex, close to 8A. Pollen amount: Moderate. Pollen color: Close to 4D. Pistils: Quantity: Typically one. Pistil length: About 2.5 cm. Style color: Close to 144D. Stigma shape: Conical. Stigma color: Close to 144C. Ovary color: Close to 144C.

*Seeds and fruits*.—Seed and fruit production have not been observed on plants of the new *Mandevilla*.

Disease & pest resistance: Plants of the new *Mandevilla* have not been noted to be resistant to pathogens and pests common to *Mandevilla* plants.

Garden performance: Plants of the new *Mandevilla* have been observed to tolerate wind, rain and temperatures ranging from about 4° C. to about 30° C.

It is claimed:

1. A new and distinct *Mandevilla* plant named 'Sunparaochoco' as illustrated and described.

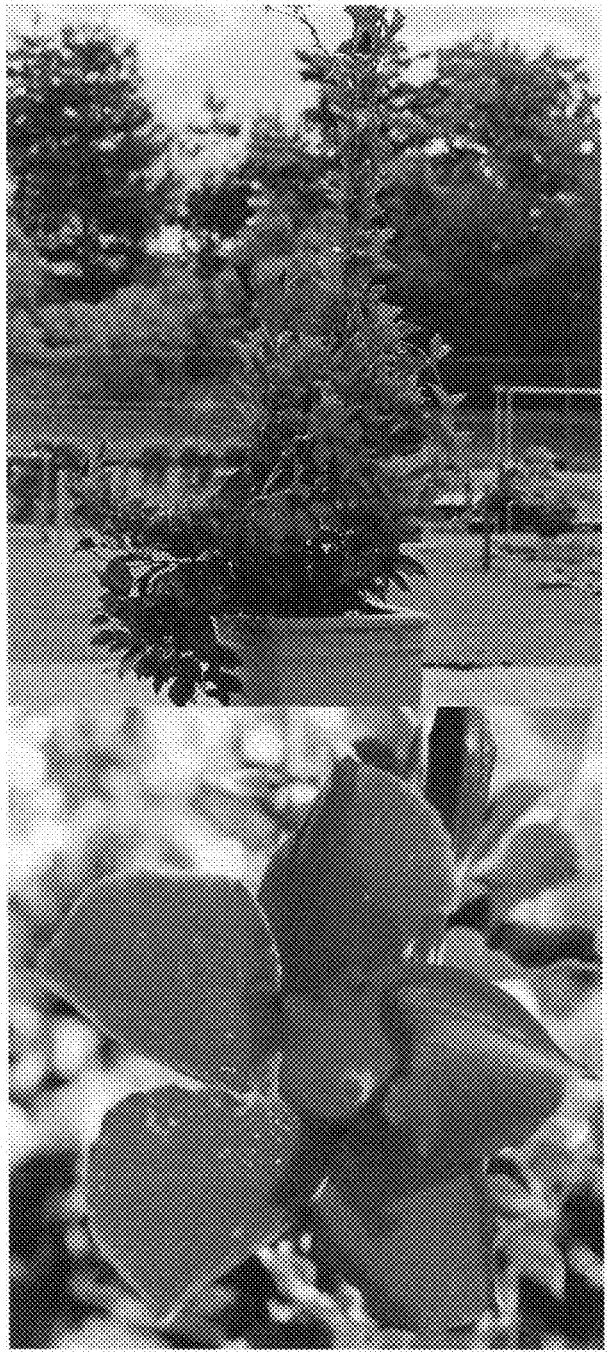

* * * * *